Figure 1:
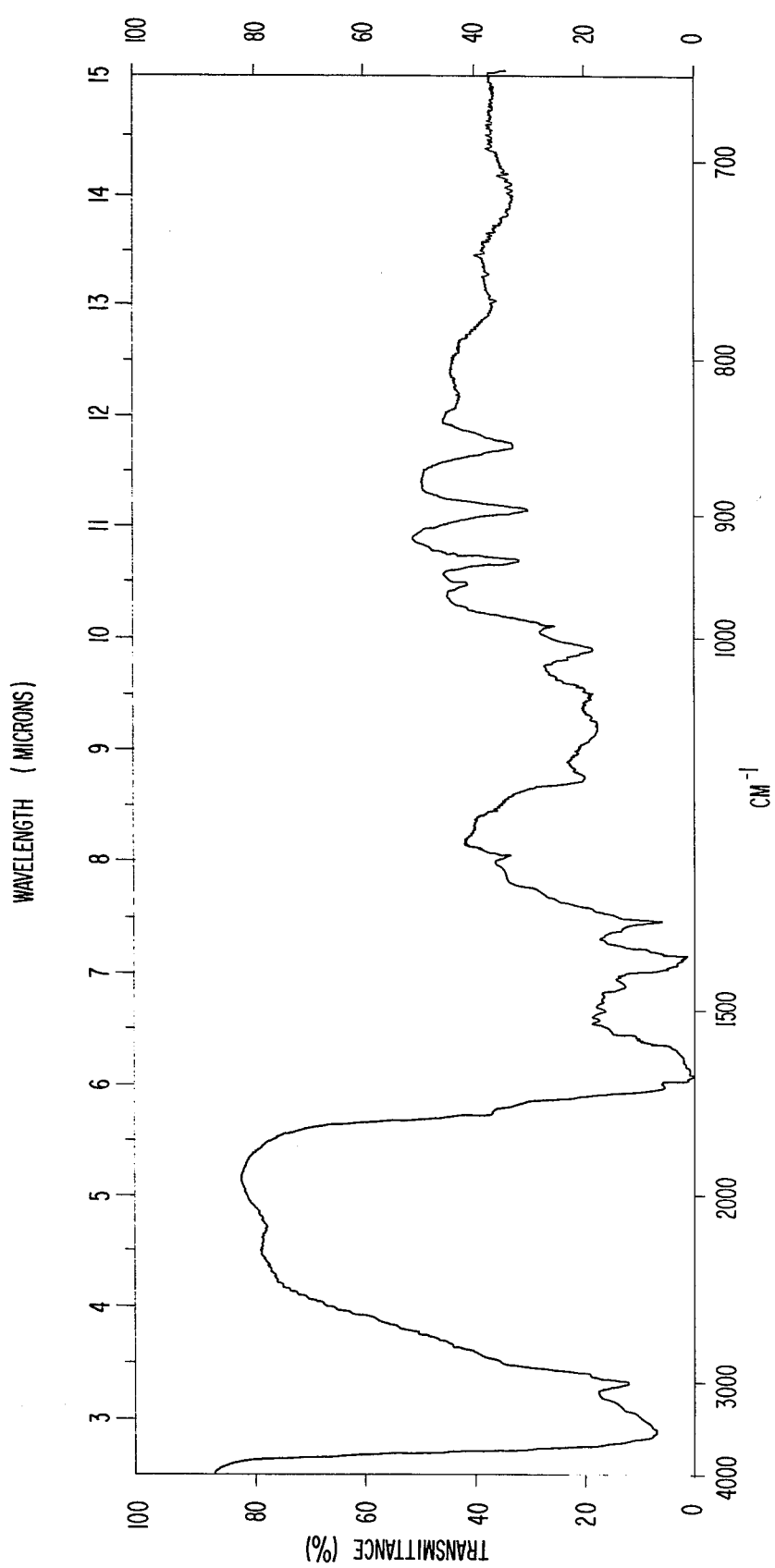

United States Patent [19]

Olson et al.

[11] 4,104,369

[45] Aug. 1, 1978

[54] LYMPHOSARCIN AND METHOD OF PRODUCING LYMPHOSARCIN

[75] Inventors: Birger H. Olson; David M. Schuurmans; Theodore R. Watson, all of Lansing; Chun-nan Shih; Burton D. Cardwell, both of East Lansing, all of Mich.

[73] Assignee: State of Michigan, Lansing, Mich.

[21] Appl. No.: 719,132

[22] Filed: Aug. 31, 1976

[51] Int. Cl.$^2$ ............................................. A61K 35/74
[52] U.S. Cl. ................................ 424/115; 195/80 R; 424/123
[58] Field of Search ............. 195/80 R; 424/115, 123, 424/124

[56] References Cited

U.S. PATENT DOCUMENTS

| 3,973,005 | 8/1976 | Rosenberg ........................... 424/115 |
| 3,992,524 | 11/1976 | Umezawa et al. ................... 424/115 |

OTHER PUBLICATIONS

International Journal of Systematic Bacteriology, vol. 18, p. 148; 1968.
Organic Chemistry; Morrison and Boyd; Second Ed., p. 152, 1966.

*Primary Examiner*—Alvin E. Tanenholtz
*Assistant Examiner*—Robert J. Warden
*Attorney, Agent, or Firm*—Bernard & Brown

[57] ABSTRACT

A new methyl pentaene, lymphosarcin, is provided by the culturing of a new strain of *Streptomyces murinus*. Lymphosarcin exhibits antineoplastic activity.

25 Claims, 3 Drawing Figures

LYMPHOSARCIN AND METHOD OF PRODUCING LYMPHOSARCIN

The present invention relates to a new methyl pentaene which has been designated lymphosarcin, and to the preparation of the same. The name lymphosarcin has been proposed to the United States Adopted Names Council. Lymphosarcin exhibits antineoplastic activity.

Lymphosarcin is a methyl pentaene produced by fermentation of an organism discovered as an isolate from a sample of soil from a grassy ocean beach in the State of New Jersey. The organism has been designated as MDPH 40886A by the Michigan Department of Public Health, located in Lansing, Mich. A culture of MDPH 40886A has been deposited with the United States Department of Agriculture, Northern Utilization Research and Development Division located in Peoria, Ill., and has been assigned the numerical designation NRRL 8171. Dry lymphosarcin has a light yellow-white color. A sample of lymphosarcin has been provided to independent laboratories for structural analysis, elemental analysis and determination of its molecular weight.

The lymphosarcin-producing organism has the characteristics of *Streptomyces murinus* as, for instance, set forth in Bergy's Manual of Determinative Bacteriology. The morphology of NRRL 8171 may be characterized as follows. The mature spore chains are usually made up of 15 to 35 spores when grown on arginine glycerol salts agar. The individual spore surface is smooth and measures 0.8 by 1.1 microns. 14 day growth on Czapeks agar plates is sparse and of an alabaster tint. Fourteen day growth on glucose asparagine agar is flat granular with raised irregular edge, and the color is lemon yellow. The aerial growth has an edge that is rosewood in color and the center is bisque light rose beige. Apparently no soluble pigment is produced on the glucose asparagine medium but on nutrient agar, and on arginine glycerol salts agar, a soluble pigment that is sulfur yellow in color is produced.

The fermentation of NRRL 8171 can be carried out in any convenient manner under aerobic conditions in an aqueous medium. The nutrient medium contains assimilable sources of carbon, nitrogen and minerals, i.e., inorganic salts. The carbon may be supplied by, for instance, any suitable carbohydrate source such as glucose, whole wheat flour, starch, dextrin, and the like. Particularly advantageous yields of lymphosarcin have been obtained employing glucose as the carbon source. The amount of carbohydrate provided in the fermentation medium may vary widely, say from about 0.5 to 15, preferably about 2 to 10, weight percent of the medium. The nitrogen source may be any suitable assimilable nitrogen-containing material and may be inorganic or, preferably, organic, e.g., amino acids. Exemplary of nitrogen sources which may be employed include yeast extract, dry milk, ammonium salts, e.g., ammonium sulfate, nitrates, and the like, and may comprise about 0.5 to 15, preferably about 1 to 10, weight percent of the medium. The minerals include minor amounts of metals suitable for promoting the growth of NRRL 8171 and may be provided by, say, sterilized tap water, yeast extract, inorganic salts, or the like. The minerals often include calcium, trace metals such as magnesium, zinc and the like in minor amounts sufficient to enhance the growth of NRRL 8171. A particularly desirable source of nitrogen and minerals is yeast extract. The yeast extract may be employed in amounts of about 0.1 to 10, preferably, about 0.2 to 4, weight percent of the medium. Up to about 90 percent of the yeast extract may be replaced by dry Brewer's yeast or the yeast extract may be partially or completely replaced with a mixture of Brewer's yeast and ammonium sulfate while obtaining good yields of lymphosarcin. Often, the Brewer's yeast may comprise about 0.05 to 5, preferably about 0.1 to 1, weight percent of the medium and the ammonium sulfate may comprise about 0.05 to 5, preferably about 0.1 to 1, weight percent of the medium. Advantageously, the medium also includes a buffer, e.g., calcium carbonate.

The medium may also contain a precursor for lymphosarcin. Suitable precursors include propionic acid and oleic acid or water-soluble salts thereof, e.g., sodium or other alkali or alkaline earth metal, and water-soluble salts of acetic acid such as sodium acetate. Precursors enhance the production of lymphosarcin by NRRL 8171. If desired, one or more of the precursors can be employed in the fermentation medium and the effect of different precursors such as the propionic or oleic precursors may be additive. Thus, for instance, a marked improvement in the production of lymphosarcin can be observed when both propionic and oleic precursors are employed as compared to employing only one of them. The oleic precursor provides significant increases in lymphosarcin yields and increases in yields of several fold have been observed using an oleic precursor. The propionic precursor and sodium acetate, for instance, provide only a slight stimulation, say, up to about 10 or 15 percent increase, in lymphosarcin yields. Each precursor employed may be added to the initial fermentation medium or it may be added one or more times during the fermentation. Advantageously, at least a portion of the precursor is added after fermentation has proceeded for about 1.5 to 2 days. Each precursor employed may be added in amounts sufficient to enhance the production of lymphosarcin. For instance, each precursor may generally be employed in amounts of about 0.01 to 1.5, preferably about 0.03 to 1, weight percent of the medium. The oleic precursor may frequently be employed in amounts of about 0.1 to 1.5, preferably about 0.3 to 1, weight percent of the medium. The propionic precursor is generally employed in lesser amounts since larger concentrations of propionate in the medium may result in undue inhibition of microorganism growth due to the toxicity of the propionate, and often the propionic precursor is provided in an amount of about 0.01 to 0.1 weight percent of the fermentation medium. Frequently the propionic precursor is added, say, after the fermentation has proceeded for about 1.5 days and the precursor is added in fractional increments over a period of time to maintain a suitable propionate level in the fermentation medium. Conventional fermentation additives such as antifoam agents may also be employed.

The fermentation may proceed at suitable fermentation temperatures which may be somewhat elevated, e.g., about 23° to 38° C. Temperatures of about 33° to 37° C. have been found particularly advantageous for the fermentation of NRRL 8171. The fermentation is advantageously conducted employing a relatively neutral pH, e.g., a pH of about 5.5 to 8.5. The fermentation can be continued for a sufficient period of time to provide recoverable amounts of lymphosarcin. Generally, the fermentation may be conducted over a period of about 20 to 200, preferably about 70 to 140, hours.

When employing submerged, aerobic fermentation, the medium is preferably agitated and oxygen-containing gas, e.g., air, is passed through the medium. The aeration rates may frequently be about 0.1 to 2 volumes of air per volume of medium per minute.

The lymphosarcin produced during fermentation is present in both the mycelial cells and in the fermentation broth. Since lymphosarcin is highly insoluble in water, it exists as a precipitate when in the fermentation broth. The lymphosarcin may be recovered from the fermentation broth in any suitable manner including extraction or filtration. The greatest portion of the lymphosarcin is in the fermentation broth as a precipitate and in the mycelia until autolysis occurs. Therefore, the lymphosarcin can conveniently be recovered by separating the solids from the fermentation broth, e.g., by filtering the whole broth. Advantageously, a filter aid, for instance, a diatomaceous earth filter aid, e.g., Celite ® 545, is employed in an amount sufficient to facilitate recovery of the lymphosarcin by filtration. The mother liquor generally contains at most very small amounts of lymphosarcin and may frequently be discarded without undue loss. If desired, any lymphosarcin remaining in the mother liquor may be recovered therefrom by extraction with a water-immiscible solvent for lymphosarcin such as butanol.

The microorganism also produces various actinomycins and pentaenes during fermentation which may also be in the solid phase. Since several of the actinomycins may be toxic, the lymphosarcin may advantageously be extracted from the separated solids and removed. The extraction of lymphosarcin may proceed by, for instance, contacting the solids with an organic solvent in which lymphosarcin is soluble, e.g., methanol. Other solvents which may be employed include ethanol, isopropanol, butanol, phenol, propionic acid, formamide, dimethyl formamide, and the like. The solvents are often comprised of carbon, hydrogen and oxygen, and may include other elements such as nitrogen. The extract may be concentrated, e.g., under vacuum, frozen and lyophilized. The extract may also contain actinomycins which may be soluble in the solvent. The actinomycins can be removed employing a solvent in which they are soluble but lymphosarcin is relatively insoluble, e.g., benzene, ethyl acetate, mixtures of a major amount of benzene and minor amount of methanol and the like. The same or different solvents can be employed in sequential extractions. The resulting lymphosarcin-containing residue may conveniently be extracted with a solvent for the lymphosarcin such as methanol, concentrated and lyophilized with a non-solvent for the lymphosarcin such as water, ethyl acetate or benzene to provide a dry lymphosarcin-containing product. This product generally contains other pentaenes produced by NRRL 8171, and may be termed crude lymphosarcin. Frequently about 50 to 95 weight percent of crude lymphosarcin is lymphosarcin with substantially the remainder being other pentaenes.

A particularly advantageous method of isolating lymphosarcin is by the simultaneous extraction of lymphosarcin obtained from the fermentation medium by contact with extracting amounts of water and ethyl acetate. The solvent may comprise water and ethyl acetate in a volume ratio of say, about 1:10 to 10:1, preferably about 1:3 to 3:1 of water to ethyl acetate, and a lymphosarcin to total solvent weight ratio of, for instance, about 0.01 to 10 or more, weights of lymphosarcin to 100 weights of total solvent is generally employed. A water extraction layer forms on the bottom and an ethyl acetate layer forms on the top with the lymphosarcin-containing material being disposed therebetween. Suitable means may be employed to enhance the separation of the water and ethyl acetate layers such as centrifuging means. Frequently, the isolation may proceed with a first separation wherein the clear water extract and ethyl acetate extract layers are removed, and the resulting lymphosarcin-containing material is centrifuged to provide a further separation of the water extract, ethyl acetate extract, and lymphosarcin-containing layers. When the lymphosarcin-containing layer is further extracted with ethyl acetate, lymphosarcin having a purity of over about 90 percent may be obtained.

Pentaenes are generally unstable, particularly in the presence of oxygen, and their degradation may be enhanced by light. The degradation of pentaenes is often accelerated when the pentaene is in pure form; however, in the presence of other pentaenes, the degradation can be significantly retarded. Lymphosarcin exhibits similar characteristics with regard to stability. Crude lymphosarcin, i.e., lymphosarcin containing other pentaenes, may have a storage life of over two years when protected from light and oxidation and stored at 0° to 6° C. Dry preparations often exhibit better stability than solutions of lymphosarcin. Highly pure lymphosarcin, e.g., 99.5 or more percent pure, can be quickly degraded, especially in the presence of light and air. Therefore, special handling of highly pure lymphosarcin fractions such as storage in dry form under an inert atmosphere, e.g., nitrogen, in a cool, dark location, should be undertaken. Lymphosarcin may be stabilized by adding an antioxidant, but as is characteristic with other pentaenes, the presence of additional pentaenes, e.g., about 5 to 50 weight percent of the total pentaene content, provides effective stabilization.

The crude lymphosarcin may be purified in any convenient manner employing highly selective separational techniques. A particularly desirable technique is through the use of high pressure liquid chromatography. A reverse phase resin column, e.g., a C-18 Corasil column obtainable from Waters Associates, may be employed for the chromatographic separation using solvents of water and of an equal volume of methanol and acetonitrile. Generally, it may be more convenient to employ the crude lymphosarcin rather than to purify the lymphosarcin; however, there may be instances when highly pure lymphosarcin is desirable.

The following examples will serve to illustrate the invention.

EXAMPLE I

Dry milk, yeast extract, calcium carbonate, and glucose are mixed with water in the following proportions to provide a fermentation medium

| | Weight Percent |
|---|---|
| Dry milk | 1 |
| Yeast extract | 1 |
| Calcium carbonate | 0.5 |
| Glucose | 2 |

Also provided in the fermentation medium is an antifoam agent, Hodag K66, available from the Hodag Chemical Corporation, which is added in three increments, i.e., initially, after one day, and after 2 days of fermentation, as needed for a total of 0.22 weight percent of the medium. Sodium oleate is added in three increments, each of 0.1 weight percent of the medium, at hours 0, 36 and 48 of fermentation. The medium has a pH of about 6.0 to 6.5, and no pH adjustment is made. The medium is sterilized with steam in a conventional manner. The resulting sterile nutrient medium is inoculated with a culture of the NRRL 8171 microorganism described above and is allowed to grow under a temperature of about 35° C. with agitation and aeration at an airflow of about 0.8 volume of air per volume of medium per minute. The fermentation is allowed to continue for about 120 hours with the additions of antifoam agent and sodium oleate in the amounts and times indicated. At the end of this period the fermentation broth is press filtered using Celite® 545 as a filter aid to remove mycelia and precipitate. The filtrate is discarded since it contains only a small amount of lymphosarcin; however, if desired, the filtrate could be extracted with a solvent for lymphosarcin such as butanol to recover any lymphosarcin values which may exist in the filtrate.

EXAMPLE II

The procedure of Example I is essentially repeated except employing the following proportions of ingredients.

|  | Weight percent |
|---|---|
| Dry milk | 1 |
| Yeast extract | 1 |
| Calcium carbonate | 0.5 |
| Cerelose (dextrose) | 6 |
| Antifoam (Hodag K66) | 0.8 |
| Sodium oleate | 0.7 |

The sodium oleate is added after 48 hours of fermentation, and the pH of the medium is adjusted to 7.0 with sodium hydroxide.

Since glucose can be broken down during sterilization, conditions during sterilization which lead to the undue breakdown of glucose are avoided.

EXAMPLE III

The procedure of Example II is essentially repeated except that 0.05 weight percent of sodium propionate is added to the medium at 48 hours of fermentation as an additional precursor. The production of lymphosarcin is increased.

EXAMPLE IV

The procedure of Example II is essentially repeated except that 0.5 weight percent Brewer's yeast and 0.5 weight percent ammonium sulfate are employed instead of the yeast extract, and lymphosarcin is produced.

EXAMPLE V

The mycelium and precipitate from Example I are removed from the press and slurried with methanol in an agitated tank. The volume of methanol is about 0.7 times the volume of the original whole culture (255 liters), i.e., about 180 liters. The methanol extract is removed by filtration and then concentrated under vacuum to yield a suspension of lymphosarcin in water. The concentrate is about 15 liters, or about 1/17th of the original whole culture volume. The concentrate is then frozen and lyophilized. Approximately 2.5 to 2.8 grams of dry material containing lymphosarcin and actinomycins are obtained from each liter of whole culture.

EXAMPLE VI

Lymphosarcin is further isolated from the crude dry material of Example V by extracting one hundred grams of the dry product with 300 ml. of benzene 80%-methanol 20% by volume to remove actinomycins in the extract phase. The solvent is removed by filtration and two additional extractions are made with 150 milliliters each of the same solvent. The residue from the last extraction is then extracted with 900 milliliters of methanol. This is done in a series of extractions employing 450 milliliters of methanol in each treatment, however, a single extraction can be used. The residue is discarded and the combined methanol extract which contains lymphosarcin and other pentaenes is concentrated to about 100 ml., diluted with 4 volumes of benzene, frozen and lyophilized to yield about 25 grams of crude lymphosarcin (about 75 percent by weight of lymphosarcin and the remainder being essentially other pentaenes). This purified (crude) lymphosarcin, when assayed against P 388 (a standard leukemia) induced in mice shows measurable life extension of the mice at dosage limits as low as 0.010 milligrams per kilogram of body weight per day. Higher doses do not show toxicity even at 10 times the effective dose.

EXAMPLE VII

The procedure of Example VI is essentially repeated except that benzene alone is used in removal of the actinomycins in the isolation of crude lymphosarcin.

EXAMPLE VIII

The procedure of Example VI is essentially repeated except that ethyl acetate first, followed by benzene, is used in removal of the actinomycins in the isolation of crude lymphosarcin.

EXAMPLE IX

Fifteen liters of lymphosarcin concentrate produced by the essentially same procedure described in Example V, which is essentially a water suspension, are analyzed to contain 88 percent of the lymphosarcin in the whole culture with the lymphosarcin being about 18.1 percent pure. The concentrate is further isolated by adding 5 liters of deaerated distilled water and 20 liters of ethyl acetate to the concentrate. The mixture is agitated thoroughly while avoiding the exposure of the mixture to excessive amounts of air or light. The mixture is allowed to settle and a water extract layer forms on the bottom, an ethyl acetate extract layer forms on the top, and the lymphosarcin-containing material is in the middle. The clear, settled extract layers are drawn off and the lymphosarcin-containing material is centrifuged, again forming a water extract layer and ethyl acetate extract layer with an intermediate lymphosarcin-containing layer. The lymphosarcin-containing layer is reextracted with 20 liters of ethyl acetate, separated and dried under vacuum. The final product recovery is determined to be 69 percent, and the purity of the lymphosarcin product is analyzed to be about 90 to 92 percent.

EXAMPLE X

The lymphosarcin of Example VI is purified by High Pressure Liquid Chromatography with a Waters Associates gradient #7. The solvent A (water) and solvent B (50% methanol and 50% acetonitrile) start at 65% and 35% respectively in this gradient. In 20 minutes of operation they change to a final ratio of solvent A — 40% and solvent B — 60%. This run is made on analytical columns of C-18 Corasil (a reverse phase resin from Waters Associates). The column is 4 feet long and has a ⅛ inch diameter. The instrument used is a Waters Associates Model 201 with ultra-violet detector at 254 nm. Highly pure lymphosarcin, i.e., at least 99.5 percent pure, is obtained.

The lymphosarcin prepared in Example VI as described above exhibits characteristic absorption bands in the infra-red region of the spectrum when compressed in a potassium bromide pellet (2.5 mg. in 200 mg.) and run in a Perkin and Elmer Infracord. See accompanying FIG. 1. The major peaks are found approximately located as follows: 3450 reciprocal centimeters, 3050 reciprocal centimeters, 1650 reciprocal centimeters and 1400 reciprocal centimeters. Minor peaks are found as follows: 1460 reciprocal centimeters, 1350 reciprocal centimeters, 1145 reciprocal centimeters, 1085 reciprocal centimeters, 1055 reciprocal centimeters, 1005 reciprocal centimeters, 970 reciprocal centimeters and 850 reciprocal centimeters.

Figure 2:
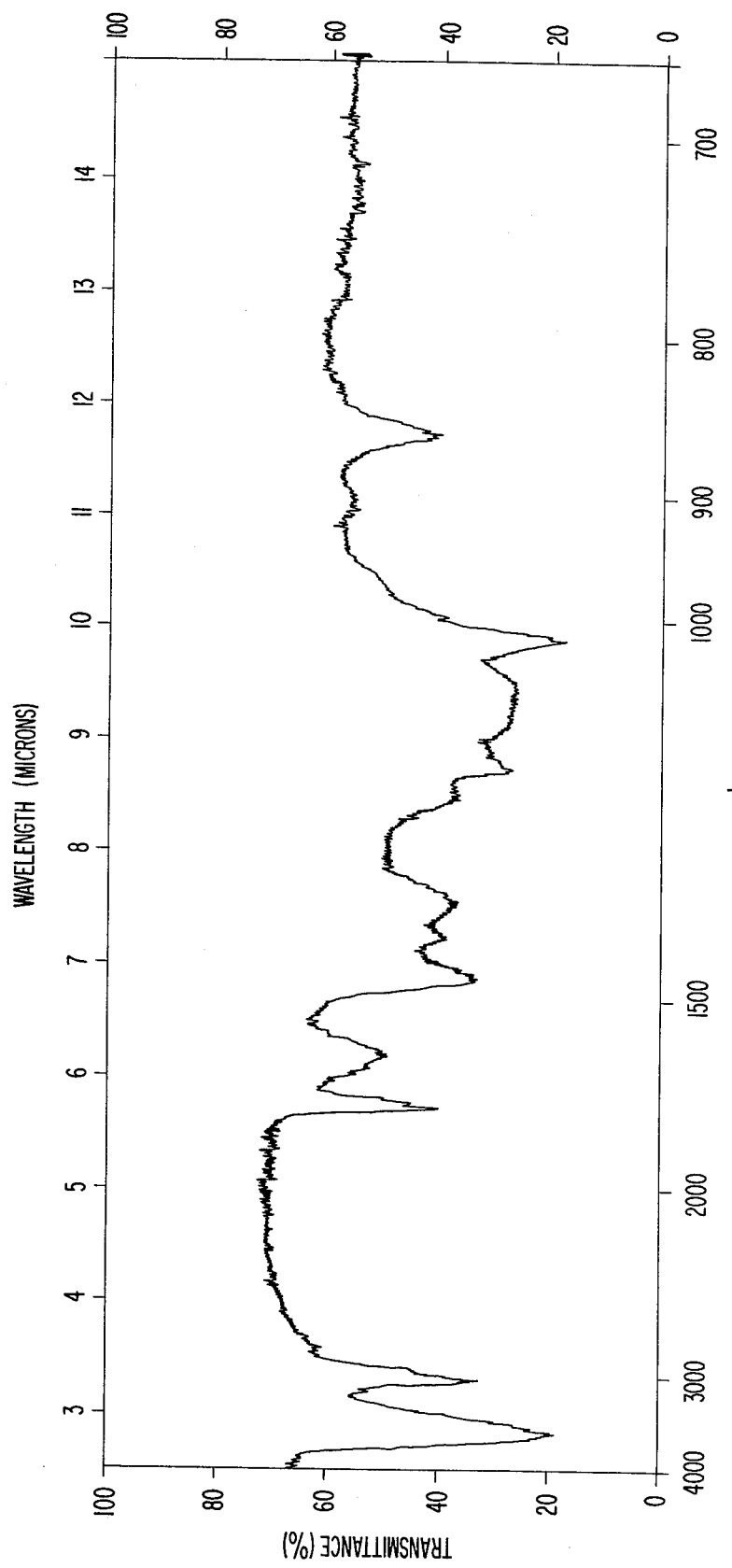

The pure lymphosarcin prepared in Example X exhibits characteristic absorption bands in the infra-red region of the spectrum when compressed in a potassium bromide pellet and run in a Perkin and Elmer Infracord as above. See accompanying FIG. 2. The major peaks are found approximately located as follows: 3450 reciprocal centimeters, 3050 reciprocal centimeters, 1460 reciprocal centimeters, 1145 reciprocal centimeters, and 1005 reciprocal centimeters. Minor peaks are found at 1750 reciprocal centimeters, 1600 reciprocal centimeters, and 1330 reciprocal centimeters.

Figure 3:
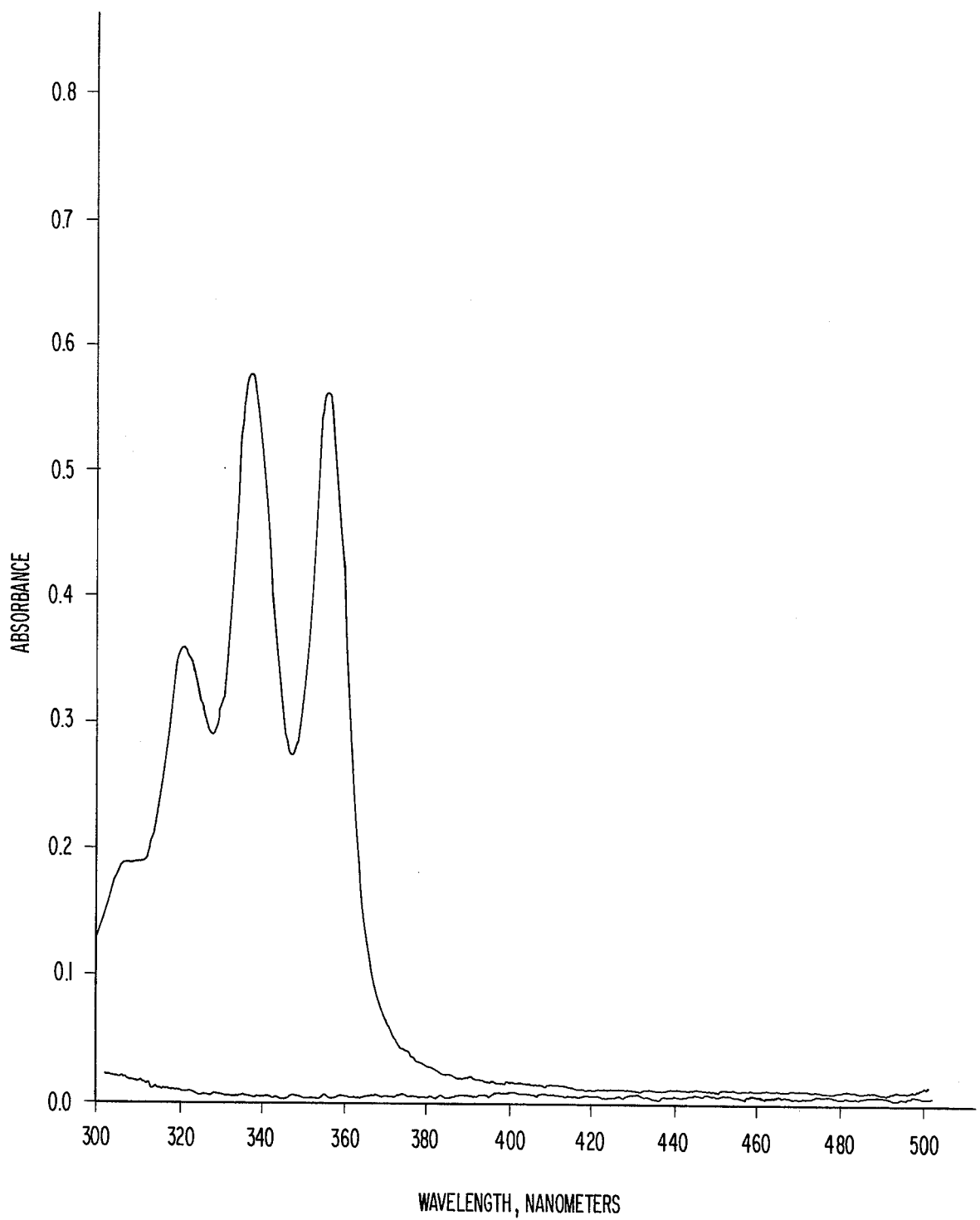

The pure lymphosarcin such as provided by Example X shows absorption in the ultra-violet region as a 0.00025 percent solution in methanol (see accompanying FIG. 3) with absorption maxima of approximately 357, 338 and 322 nanometers with a shoulder in the area of 305 nanometers. The ultraviolet spectra is indicative of a methyl pentaene. Crude lymphosarcin, e.g., the lymphosarcin prepared by the procedure of Example VI, exhibits a similar ultraviolet absorption spectrum.

Lymphosarcin is soluble in methanol, ethanol, butanol, phenol, tricresol, ethylene glycol, propylene glycol, pyridine, formamide, dimethyl formamide, and propionic acid; has limited solubility in isopropyl alcohol and tetrahydrofuran; and is insoluble in water, diethyl ether, petroleum ether, benzene, acetone, ethyl acetate, and acetonitrile.

Pharmaceutical compositions containing lymphosarcin, i.e., ether crude lymphosarcin or pure lymphosarcin, can be administered to a host in any convenient manner in an amount sufficient to provide antineoplastic or anti-tumor activity, and may be in admixture with a pharmaceutically-acceptable solid or liquid carrier. For example, lymphosarcin may be administered by the parenteral administration, e.g., by intravenous, intramuscular, intraperitoneal, and the like, injections. Generally, the amount of lymphosarcin administered to an animal to achieve antineoplastic activity is about 0.001 to 1, preferably 0.005 to 0.5, milligrams per kilogram of body weight per day. Lymphosarcin may be administered periodically from, say 1 or 2 times a week to 2 or 3 times a day or more.

Lymphosarcin may be suspended in or dissolved in liquid vehicles suitable for administration. The final preparation may be in the form of a solution, emulsion, suspension, syrup, or the like. Liquid carriers which may be employed include, for instance, peanut oil, sesame oil, olive oil, water, liquid paraffins, propylene glycol, polyethylene glycol and the like. A particularly desirable carrier comprises a minor amount of ethanol and propylene glycol. The liquid preparations may also contain wetting, emulsifying, or dispersing agents and other conventional additions for liquid pharmaceutical dosage forms. The lymphosarcin may be in combination with other pentaenes or stabilizing agents to retard degradation. It will be understood that lymphosarcin as used to treat neoplasms can be brought into unit dosage form by any suitable technique.

Lymphosarcin, the product of the present invention, has been found to have antitumor activity in certain induced tumors (various types of leukemia and melanoma) in animals. The animals used for the evaluation against induced tumors have largely been mice. However, in addition to the tests done in mice, the Michigan Department of Health Laboratories have also found that lymphosarcin is capable of effecting change in naturally occurring tumors in dogs. Dogs with lymphosarcoma has been treated and the life of the dogs has been extended. It has been found that lymphosarcin is active against feline leukemia virus in a cat.

The following examples further illustrate the antineoplastic activity of lymphosarcin.

EXAMPLE XI

When the dog enters the clinic a biopsy is taken and a pathologic diagnosis is made. Treatment is then initiated at a dosage level of 0.05 milligram of crude lymphosarcin (75% lymphosarcin) per kilogram of body weight intravenously administered in an ethanol and propylene glycol carrier approximately 3 times per week and the size of the tumors is recorded. The usual course of a lymphosarcoma dog, without previous treatment, at the stage of disease seen when entering the clinic would be death in less than 4 weeks. The course of disease when the dog is treated with lymphosarcin is for the tumors to regress in 3 to 4 weeks and then disappear completely, and for the dog to be returned to its owner in 7 weeks.

EXAMPLE XII

Lymphosarcin such as provided by the procedure of Example VI is screened in accordance with the standard procedure of the Division of Cancer Treatment of the National Cancer Institute for antineoplastic activity against induced tumors in mice. The tumors induced are P 388 (leukemia), B 16 (melanoma) and L 1210 (lymphoic leukemia). Lymphosarcin is intraperitoneally injected at various dosage levels and frequencies. The results are summarized in the following tables in which mg/kg represents milligrams per kilogram of body weight per day, the day of evaluation is the number of days after the first injection, the tumor evaluation is by the procedure described in Cancer Chemotherapy Reports, Part 3 of Volume 3, No. 2, September, 1972, and Percent (T/C) is the ratio of the tumor evaluations of the test and control animals expressed in percent.

TABLE 1

L-1210 Screen

| Run | No. Initially | Mice Survivors | Dose/Injection mg/kg | Frequency of Injections, days | No. of Doses | Day of Evaluation | Tumor Test | Evaluation Control | Percent (T/C) |
|---|---|---|---|---|---|---|---|---|---|
| 1 | 6 | 6 | 4 | 4 | 3 | 30 | 10.3 | 9.5 | 108 |
| 2 | 6 | 6 | 2 | 4 | 3 | 30 | 10.3 | 9.5 | 108 |
| 3 | 6 | 6 | 1 | 4 | 3 | 30 | 11.3 | 9.5 | 118 |
| 4 | 6 | 6 | 0.5 | 4 | 3 | 30 | 9.8 | 9.5 | 103 |
| 5 | 6 | 6 | 2 | 1 | 9 | 20 | 12.2 | 9.8 | 124 |
| 6 | 6 | 6 | 1 | 1 | 9 | 20 | 11.2 | 9.8 | 114 |
| 7 | 6 | 6 | 0.5 | 1 | 9 | 20 | 11.3 | 9.8 | 115 |
| 8 | 6 | 6 | 0.25 | 1 | 9 | 20 | 10.7 | 9.8 | 109 |
| 9 | 6 | 4 | 8 | 1 | 9 | 30 | 6.0 | 9.4 | — |
| 10 | 6 | 6 | 4 | 1 | 9 | 30 | 7.2 | 9.4 | — |
| 11 | 6 | 6 | 2 | 1 | 9 | 30 | 12.3 | 9.4 | 130 |
| 12 | 6 | 6 | 1 | 1 | 9 | 30 | 11.5 | 9.4 | 122 |
| 13 | 6 | 5 | 0.5 | 1 | 9 | 30 | 11.0 | 9.4 | 117 |
| 14 | 6 | 6 | 0.25 | 1 | 9 | 30 | 11.0 | 9.4 | 117 |
| 15 | 8 | 8 | 13.3 | 4 | 3 | 45 | 10.0 | 8.9 | 112 |
| 16 | 8 | 8 | 8 | 4 | 3 | 45 | 10.9 | 8.9 | 122 |
| 17 | 8 | 8 | 4.8 | 4 | 3 | 45 | 10.9 | 8.9 | 122 |
| 18 | 8 | 8 | 2.88 | 4 | 3 | 45 | 10.1 | 8.9 | 113 |
| 19 | 8 | 8 | 13.3 | 4 | 3 | 45 | 13.3 | 13.3 | 100 |
| 20 | 7 | 7 | 8 | 4 | 3 | 45 | 13.7 | 13.3 | 103 |
| 21[a] | 8 | 8 | 4.8 | 4 | 3 | 45 | 21.9 | 13.3 | 164 |
| 22[b] | 8 | 8 | 2.88 | 4 | 3 | 45 | 16.8 | 13.3 | 126 |
| 23 | 8 | 8 | 13.3 | 4 | 3 | 45 | 9.1 | 8.3 | 109 |
| 24 | 8 | 8 | 8 | 4 | 3 | 45 | 9.5 | 8.3 | 114 |
| 25 | 8 | 8 | 4.8 | 4 | 3 | 45 | 8.9 | 8.3 | 107 |
| 26 | 8 | 8 | 2.88 | 4 | 3 | 45 | 8.8 | 8.3 | 106 |
| 27 | 8 | 8 | 13.3 | 4 | 3 | 45 | 11.1 | 12.0 | 92 |
| 28 | 8 | 8 | 8 | 4 | 3 | 45 | 12.4 | 12.0 | 103 |
| 29 | 8 | 8 | 4.8 | 4 | 3 | 45 | 12.6 | 12.0 | 105 |
| 30 | 8 | 8 | 2.88 | 4 | 3 | 45 | 11.9 | 12.0 | 99 |

[a] Two cures are observed
[b] One cure is observed.

TABLE 2

B 16 Screen

| Run | No. Initially | Mice Survivors | Dose/Injection mg/kg | Frequency of Injections, days | No. of Doses | Day of Evaluation | Tumor Test | Evaluation Control | Percent (T/C) |
|---|---|---|---|---|---|---|---|---|---|
| 1 | 10 | 0 | 8 | 1 | 9 | 60 | 5.1 | 14.3 | — |
| 2 | 10 | 10 | 4 | 1 | 9 | 60 | 8.8 | 14.3 | — |
| 3 | 10 | 10 | 2 | 1 | 9 | 60 | 19.0 | 14.3 | 132 |
| 4 | 10 | 10 | 1 | 1 | 9 | 60 | 24.0 | 14.3 | 167 |
| 5 | 10 | 10 | 0.5 | 1 | 9 | 60 | 25.3 | 14.3 | 176 |
| 6 | 10 | 10 | 0.25 | 1 | 9 | 60 | 20.3 | 14.3 | 141 |
| 7 | 10 | 9 | 4 | 1 | 9 | 60 | 9.7 | 16.8 | — |
| 8 | 10 | 9 | 2 | 1 | 9 | 60 | 27.8 | 16.8 | 165 |
| 9 | 10 | 10 | 1 | 1 | 9 | 60 | 25.0 | 16.8 | 148 |
| 10 | 10 | 10 | 0.5 | 1 | 9 | 60 | 25.3 | 16.8 | 150 |
| 11 | 10 | 10 | 0.25 | 1 | 9 | 60 | 21.0 | 16.8 | 125 |
| 12 | 10 | 10 | 0.12 | 1 | 9 | 60 | 20.3 | 16.8 | 120 |
| 13 | 10 | 10 | 0.06 | 1 | 9 | 60 | 20.8 | 16.8 | 123 |
| 14 | 10 | 10 | 8 | 4 | 3 | 60 | 30.3 | 22.3 | 135 |
| 15 | 10 | 10 | 4 | 4 | 3 | 60 | 26.0 | 22.3 | 116 |
| 16 | 10 | 10 | 2 | 4 | 3 | 60 | 25.0 | 22.3 | 112 |
| 17 | 10 | 10 | 1 | 4 | 3 | 60 | 25.0 | 22.3 | 112 |
| 18 | 10 | 10 | 4 | 1 | 9 | 45 | 30.0 | 17.1 | 175 |
| 19 | 10 | 10 | 2 | 1 | 9 | 45 | 27.0 | 17.1 | 157 |
| 20 | 10 | 10 | 1 | 1 | 9 | 45 | 24.8 | 17.1 | 145 |
| 21 | 10 | 9 | 0.5 | 1 | 9 | 45 | 20.0 | 17.1 | 116 |
| 22 | 10 | 10 | 0.25 | 1 | 9 | 45 | 20.8 | 17.1 | 121 |
| 23 | 10 | 10 | 0.12 | 1 | 9 | 45 | 20.6 | 17.1 | 120 |
| 24 | 10 | 10 | 0.06 | 1 | 9 | 45 | 19.8 | 17.1 | 115 |
| 25[a] | 10 | 10 | 2 | 1 | 9 | 60 | 35.0 | 25.8 | 135 |
| 26[b] | 10 | 10 | 1 | 1 | 9 | 60 | 36.0 | 25.8 | 139 |
| 27[c] | 10 | 10 | 0.5 | 1 | 9 | 60 | 32.0 | 25.8 | 124 |
| 28 | 10 | 10 | 0.25 | 1 | 9 | 60 | 34.0 | 25.8 | 131 |

[a] One cure is observed
[b] One cure is observed
[c] One cure is observed

TABLE 3

P-388 Screen

| Run | No. Initially | Mice Survivors | Dose/Injection mg/kg | Frequency of Injections, days | No. of Doses | Day of Evaluation | Tumor Test | Evaluation Control | Percent (T/C) |
|---|---|---|---|---|---|---|---|---|---|
| 1 | 10 | 4 | 4 | 3 per day | 8 | 60 | 5.4 | 10.5 | — |
| 2 | 10 | 10 | 2 | " | 8 | 60 | 23.3 | 10.5 | 221 |
| 3 | 10 | 10 | 1 | " | 8 | 60 | 17.7 | 10.5 | 168 |
| 4 | 10 | 10 | 0.5 | " | 8 | 60 | 16.0 | 10.5 | 152 |
| 5 | 10 | 10 | 0.25 | " | 8 | 60 | 15.1 | 10.5 | 143 |
| 6 | 10 | 10 | 0.0 | " | 8 | 60 | 11.9 | 10.5 | 113 |
| 7 | 10 | 10 | 1 | 3 per 4 days | 24 | 60 | 21.8 | 10.5 | 207 |
| 8 | 10 | 10 | 0.5 | " | 24 | 60 | 18.9 | 10.5 | 180 |
| 9 | 10 | 10 | 0.25 | " | 24 | 60 | 17.3 | 10.5 | 164 |
| 10 | 10 | 10 | 0.12 | " | 24 | 60 | 15.8 | 10.5 | 150 |

TABLE 3-continued

P-388 Screen

| Run | No. Initially | Mice Survivors | Dose/Injection mg/kg | Frequency of Injections, days | No. of Doses | Day of Evaluation | Tumor Test | Evaluation Control | Percent (T/C) |
|---|---|---|---|---|---|---|---|---|---|
| 11 | 10 | 10 | 0.06 | " | 24 | 60 | 14.3 | 10.5 | 136 |
| 12 | 10 | 9 | 0.0 | " | 24 | 60 | 12.6 | 10.5 | 120 |
| 13 | 10 | 10 | 2 | 3 per 8 days | 16 | 60 | 27.0 | 10.5 | 257 |
| 14 | 10 | 10 | 1 | " | 16 | 60 | 22.7 | 10.5 | 216 |
| 15 | 10 | 10 | 0.5 | " | 16 | 60 | 16.4 | 10.5 | 156 |
| 16 | 9 | 9 | 0.25 | " | 16 | 60 | 15.3 | 10.5 | 145 |
| 17 | 10 | 10 | 0.12 | " | 16 | 60 | 14.1 | 10.5 | 134 |
| 18 | 10 | 10 | 0.00 | " | 16 | 60 | 12.2 | 10.5 | 116 |
| 19[a] | 10 | 10 | 4 | 1 | 9 | 60 | 23.8 | 10.5 | 226 |
| 20[b] | 10 | 10 | 2 | 1 | 9 | 60 | 24.0 | 10.5 | 228 |
| 21 | 10 | 10 | 1 | 1 | 9 | 60 | 19.0 | 10.5 | 180 |
| 22 | 10 | 10 | 0.5 | 1 | 9 | 60 | 16.1 | 10.5 | 153 |
| 23 | 10 | 10 | 0.25 | 1 | 9 | 60 | 15.8 | 10.5 | 50 |
| 24 | 10 | 10 | 0.0 | 1 | 9 | 60 | 11.0 | 10.5 | 104 |
| 25 | 10 | 10 | 8 | 4 | 3 | 60 | 22.0 | 10.5 | 209 |
| 26[c] | 10 | 10 | 4 | 4 | 3 | 60 | 19.0 | 10.5 | 180 |
| 27[d] | 10 | 10 | 2 | 4 | 3 | 60 | 16.4 | 10.5 | 156 |
| 28 | 10 | 10 | 1 | 4 | 3 | 60 | 14.9 | 10.5 | 141 |
| 29 | 10 | 10 | 0.5 | 4 | 3 | 60 | 13.3 | 10.5 | 126 |
| 30 | 10 | 10 | 0.0 | 4 | 3 | 60 | 11.4 | 10.5 | 108 |
| 31 | 10 | 5 | 16 | 8 | 2 | 60 | 9.0 | 10.5 | — |
| 32 | 10 | 10 | 8 | 8 | 2 | 60 | 17.0 | 10.5 | 161 |
| 33 | 10 | 10 | 4 | 8 | 2 | 60 | 16.4 | 10.5 | 156 |
| 34 | 10 | 10 | 2 | 8 | 2 | 60 | 13.8 | 10.5 | 131 |
| 35 | 10 | 9 | 1 | 8 | 2 | 60 | 15.3 | 10.5 | 145 |
| 36 | 10 | 10 | 0.0 | 8 | 2 | 60 | 10.8 | 10.5 | 102 |

[a]Two cures are observed
[b]One cure is observed
[c]One cure is observed
[d]One cure is observed A value for Percent (T/C) of above about 135 is significant for treating B 16 melanoma. Values for Percent (T/C) of above about 125 are significant for treating P 388 leukemia and L 1210 leukemia. When, in treating the above induced tumors, a cure is observed or the value for Percent (T/C) is above about 200, the substance is generally considered to be very effective.

It is claimed:

1. Lymphosarcin, a methyl pentaene which in methanol has absorption maxima at approximately 322, 338, and 357 nanometers in the ultraviolet spectrum; which in a potassium bromide pellet has major absorption maxima at approximately 3450, 3050, 1460, 1145, and 1005 reciprocal centimeters in the infrared spectrum; and which is soluble in methanol, ethanol, butanol, phenol, formamide, dimethyl formamide, and propionic acid; has limited solubility in isopropyl alcohol and tetrahydrofuran; and is insoluble in water, diethyl ether, petroleum ether, benzene, acetone, ethyl acetate, and acetonitrile.

2. A process for the preparation of lymphosarcin comprising cultivating *Streptomyces murinus* NRRL 8171 under aerobic conditions in an aqueous nutrient medium containing available sources of carbon, nitrogen and minerals to produce lymphosarcin in the medium, and recovering lymphosarcin therefrom.

3. The process of claim 2 wherein the cultivation is conducted under submerged, aerobic conditions at about 23° to 38° C.

4. The process of claim 3 wherein a precursor for lymphosarcin is added to the nutrient medium in an amount sufficient to enhance the production of lymphosarcin.

5. The process of claim 4 wherein the precursor comprises propionic acid or water-soluble salt thereof in an amount of about 0.01 to 0.1 weight percent of the medium.

6. The process of claim 4 wherein the carbon source is carbohydrate and is about 0.5 to 15 weight percent of the medium, and the nitrogen source comprises about 0.5 to 15 weight percent of the medium.

7. The process of claim 6 wherein the medium contains ammonium sulfate as a nitrogen source.

8. The process of claim 7 wherein the medium contains Brewer's yeast in an amount of about 0.05 to 5 weight percent of the medium.

9. The process of claim 6 wherein the medium contains yeast extract as a nitrogen source.

10. The process of claim 6 wherein glucose is a carbon source, dry milk and ammonium sulfate are nitrogen sources, and the medium contains Brewer's yeast in an amount of about 0.05 to 5 weight percent of the medium.

11. The process of claim 4 wherein the precursor comprises oleic acid or water-soluble salt thereof in an amount of about 0.1 to 1.5 weight percent of the medium.

12. The process of claim 11 wherein the cultivation is at about 33° to 37° C. and at least a portion of the oleic acid or salt thereof is added to the medium between about 1.5 to 2 days of cultivation.

13. The process of claim 11 wherein the precursor also contains propionic acid or water-soluble salt thereof in an amount of about 0.01 to 0.1 weight percent of the medium.

14. The process of claim 13 wherein the cultivation is at a temperature of about 33° to 37° C. and at least a portion of the precursor is added to the medium between about 1.5 to 2 days of cultivation.

15. A process for recovering lymphosarcin from the aqueous medium of claim 2 which contains lymphosarcin and actinomycins produced by streptomyces murinus NRRL 8171 comprising removing mycelia and precipitated solids from the aqueous medium, extracting lymphosarcin from the solids by extraction using an organic solvent in which lymphosarcin is soluble and removing the solvent from the extract to provide a lymphosarcin-containing material, and extracting actinomycins from the lymphosarcin-containing material in a solvent for actinomycins in which lymphosarcin is insoluble to provide a lymphosarcin-containing solid residue.

16. The process of claim 15 wherein the mycelia and precipitated solids are removed from the aqueous medium by filtration and a filter aid is employed.

17. The process of claim 16 wherein the filter aid is a diatomaceous earth and is employed in an amount sufficient to facilitate the filtration.

18. The process of claim 15 wherein the solvent for lymphosarcin is methanol, and the solvent for actinomycins comprises benzene or ethyl acetate, and lymphosarcin is extracted from the lymphosarcin-containing residue with methanol and the methanol is removed to provide a lymphosarcin-containing product.

19. A process for recovering lymphosarcin from the aqueous medium of claim 2 which contains lymphosarcin and actinomycins produced by streptomyces murinus NRRL 8171 comprising removing mycelia and precipitated solids from the aqueous medium to provide a lymphosarcin-containing concentrate, contacting said concentrate with extracting amounts of water and ethyl acetate to form a lower water extract layer, an upper ethyl acetate extract layer and an intermediate lymphosarcin-containing layer, and recovering lymphosarcin from the intermediate lymphosarcin-containing layer.

20. Lymphosarcin produced by the process of claim 19.

21. The product of the process of claim 2.

22. A process for treating cancer in animals which comprises administering a therapeutically effective amount of lymphosarcin to an affected animal.

23. A process as recited in claim 22 in which said therapeutically effective amount is about 0.001 to 1 milligrams per kilogram of body weight of said affected animal per day.

24. A process as recited in claim 22 in which said therapeutically effective amount is from about 0.005 to 0.5 milligrams per kilogram of body weight of said affected animal per day.

25. A process as recited in claim 22 in which lymphosarcin is administered to said affected animal parenterally in admixture with a pharmaceutically-acceptable carrier.

* * * * *